(12) United States Patent
Asah et al.

(10) Patent No.: US 6,190,376 B1
(45) Date of Patent: Feb. 20, 2001

(54) APPARATUS FOR TISSUE TREATMENT

(75) Inventors: Bjarne Asah, Taastrup; Olav Balle-Petersen, Humlebaek; Casper Dolleris, Frederiksberg C., all of (DK)

(73) Assignee: Asah Medico A/S, Hvidovre (DK)

( * ) Notice: Under 35 U.S.C. 154(b), the term of this patent shall be extended for 0 days.

(21) Appl. No.: 09/179,559

(22) Filed: Oct. 27, 1998

Related U.S. Application Data (63) Continuation-in-part of application No. 08/811,728, filed on Mar. 6, 1997, now abandoned, and a continuation of application No. PCT/DK97/00560, filed on Dec. 10, 1997.

(30) Foreign Application Priority Data

Dec. 10, 1996 (DK) .................................................. 1415/96

(51) Int. Cl.$^7$ .................................................. A61B 18/18
(52) U.S. Cl. .................................. 606/9; 606/11; 606/18
(58) Field of Search ................................ 606/9–11, 17–18

(56) References Cited

U.S. PATENT DOCUMENTS

| | | |
|---|---|---|
| 3,699,950 | 10/1972 | Humphrey, Jr. et al. . |
| 4,587,396 | 5/1986 | Rubin . |
| 4,665,913 | 5/1987 | L'Esperance, Jr. . |
| 4,717,238 * | 1/1988 | Sakuragi et al. .................. 350/96.34 |
| 4,733,660 | 3/1988 | Itzkan . |
| 4,830,462 | 5/1989 | Karny et al. . |
| 4,941,082 * | 7/1990 | Pailthorp et al. ............... 364/167.01 |
| 5,065,515 | 11/1991 | Iderosa . |
| 5,312,395 * | 5/1994 | Tan et al. .................................. 606/9 |
| 5,336,217 | 8/1994 | Buys et al. . |
| 5,411,502 | 5/1995 | Zair . |
| 5,474,549 | 12/1995 | Ortiz et al. . |
| 5,520,679 | 5/1996 | Lin . |
| 5,558,666 | 9/1996 | Dewey et al. . |
| 5,582,752 | 12/1996 | Zair . |
| 5,588,428 * | 12/1996 | Smith et al. . |
| 5,595,568 | 1/1997 | Anderson et al. . |
| 5,618,285 | 4/1997 | Zair . |
| 5,653,706 * | 8/1997 | Zavislan et al. .......................... 606/9 |
| 5,735,844 | 4/1998 | Anderson et al. . |
| 5,785,704 * | 7/1998 | Bille et al. .............................. 606/17 |
| 5,906,609 * | 5/1999 | Assa et al. ............................... 606/9 |
| 5,957,915 * | 9/1999 | Trost ..................................... 606/13 |

FOREIGN PATENT DOCUMENTS

| | | |
|---|---|---|
| 105706 | 4/1984 | (EP) . |
| 208175 | 1/1987 | (EP) . |
| 0 588078 A2 | 3/1994 | (EP) . |
| 724866 A1 | 8/1996 | (EP) . |
| WO 9401374 | 1/1994 | (WO) . |
| WO 9519147 | 7/1995 | (WO) . |

* cited by examiner

Primary Examiner—Linda C. M. Dvorak
Assistant Examiner—Roy Gibson
(74) Attorney, Agent, or Firm—Birch, Stewart, Kolasch & Birch, LLP (57) ABSTRACT

A handpiece for cosmetic tissue treatment includes an input connector for connection of a first beam-outlet end of a first optical fiber to the handpiece and for alignment of the first optical fiber with an axis of the handpiece so that a first light beam emitted from the first beam-outlet end is transmitted substantially along the axis, a movable first deflecting device for deflection of the first light beam into a second light beam, and an output for emission of the second light beam towards a target surface. The handpiece may be used for ablating a thin epidermal layer of the derma of a patient and also marks on the tissue such as marks from chloasma, liver spots, red spots, tattoos, blood vessels just below the surface, etc. In addition, warts, wounds, hair follicles, etc., may be ablated or treated.

44 Claims, 9 Drawing Sheets

APPARATUS FOR TISSUE TREATMENT

This application is a Continuation-In-Part of application Ser. No. 08/811,728 filed on Mar. 6, 1997 and now abandoned, and is also a Continuation of PCT international application No. PCT/DK97/00560 which has an international filing date of Dec. 10, 1997 which designated the United States. The entire contents of both applications are hereby incorporated by reference.

FIELD OF THE INVENTION

The present invention relates to an apparatus for tissue treatment, such as for cosmetic tissue treatment, and more particularly to a handpiece for a tissue treatment apparatus comprising a light source.

BACKGROUND OF THE INVENTION

It is known to utilise laser light for tissue treatment.

During tissue treatment, a laser ablates a thin epidermal layer of the derma of a patient. During healing, a new epidermal layer is formed on the ablated surface having the look of the derma of a young person, i.e. the new epidermal layer is formed without previously existing scars, wrinkles, etc.

Lasers that operate at a wavelength that is absorbed in water are used for tissue treatment. When the laser power density (W/mm2) at illuminated cells is sufficient, cellular water is superheated causing small explosions that disrupt heated cells.

During removal of an epidermal layer, it is essential not to damage underlying or surrounding tissue. Residual heat may cause non-ablated cells to char and become necrotic, whereby new scars may be formed and thus, it is desirable to apply laser power for a short time, to minimize transmission of conducted heat to underlying and surrounding tissue.

It is therefore desired to accurately control the amount of light energy transferred to derma to be ablated. The amount of energy must be sufficient for the dermal cells to vaporize and, simultaneously, the amount of residual energy heating non-ablated cells must be so low that non-ablated cells will not be damaged.

Apparatuses for tissue treatment are known, comprising a CO2 laser emitting a laser beam and a laser articulating arm with mirrors for reflection of the laser beam, so that the laser beam is transmitted inside the articulating arm. Further, the arm has a number of joints, so that the arm can be moved around by an operator. A handpiece to be held by the operator is connected to the arm. The laser beam is moved or scanned across a target surface by movable mirrors connected to motors and mounted in the arm. The scan pattern of the laser beam is an archimedes spiral. The laser spot formed by the laser beam on the target surface moves along the spiral at a constant angular speed.

It is a disadvantage of the known apparatus that the energy density delivered to the target surface is non-uniform across the scanned surface area of the spiral, as more energy is delivered at the centre of the spiral than at the circumferential of the spiral.

It is another disadvantage of the known apparatus that the circular outline of the scan pattern leads to non-uniform scanning of an area that is larger than the area of the scan spiral as either 1) areas that have not been scanned will remain on the surface, when abutting spirals or 2) ablated areas will be scanned more than once, due to overlap of spirals.

It is yet another disadvantage of the known apparatus that evaporated derma is exhausted through the internal of the laser articulation arm, whereby optics and other members in the arm get dirty.

It is still another disadvantage of the known apparatus that it is very laborious to disassemble members, that may have been in contact with a patient, from the handpiece, e.g., for autoclaving.

It is still another disadvantage of the known apparatus that movement of the handpiece is restrained by the laser articulation arm, as the construction of tubes interconnected by joints is not fully flexible.

In addition, these apparatus typically have large mass and a large inertia (typically also due to counter-balancing masses) which makes the operation and movement of the arm difficult and heavy.

Under the name Uni-laser 450P, Asah Medico A/S, Denmark, markets an apparatus for cosmetic tissue treatment, comprising a CO2 laser and an optical fiber coupled to the laser at one end and to a handpiece at the other end.

It is a disadvantage of this known apparatus that the laser beam is manually scanned across the target surface whereby the quality of the treatment is determined and limited by the skill of the operator.

SUMMARY OF THE INVENTION

It is an object of the present invention to provide an apparatus for tissue treatment that is adapted to automatically and accurately ablate dermal cells to a desired depth causing only a minimum of damage to cells that are not removed.

It is another object of the present invention to provide an apparatus for tissue treatment that is adapted to ablate dermal cells uniformly and from a large area of a patient.

It is a further object of the present invention to provide an apparatus for tissue treatment, having a handpiece that can be moved around, i.e. traversed and rotated, freely by an operator, i.e. without exerting forces acting against the movement.

According to a first aspect of the invention, the above-mentioned and other objects are fulfilled by a handpiece for tissue treatment, comprising an input connector for connection of a first beam-outlet end of a first optical fiber to the handpiece and for alignment of the first optical fiber with an axis of the handpiece so that a first light beam emitted from the first beam-outlet end is transmitted substantially along the axis. The handpiece further comprises movable first deflecting means for deflection of the first light beam emitted from the first beam-outlet end of the first optical fiber into a second light beam, and an output for emission of the second light beam towards a target surface.

According to a second aspect of the invention, an apparatus for tissue treatment is provided, comprising a handpiece as described above. The apparatus further comprises a light source for emission of a light beam and being connected to the handpiece with an optical fiber for transmission of the light beam to the handpiece.

When the handpiece is kept in a fixed position in relation to a target surface that is illuminated by the second light beam changing of the position of the deflecting means causes the second light beam to traverse or scan the target surface along a curve. An area may be traversed or scanned by the second light beam, e.g. by letting the second light beam traverse or scan a meander like curve substantially covering the area or, by traversing or scanning the area line by line. In the present context, the type, number and shape of curves traversed by the second light beam in order to traverse a specific area is denoted the traversing pattern or the scan pattern. The area that is scanned or traversed by the second light beam is denoted the scan area, the treatment area or the traversed area.

Cellular water absorbs light energy, and applying light energy to the cells is therefore an efficient way of ablating tissue. Thus, it is preferred to use light sources, such as lasers, generating light at wavelengths with a high absorption in water, preferably wavelengths larger than 190 nm, such as wavelengths in the range from 190 nm to 1900 nm, preferably from 700 nm to 900 nm, and even more preferred approximately 810 nm, or, preferably wavelengths larger than 1900 nm, such as wavelengths in the range from 1900 nm to 3000 nm, preferably from 1900 nm to 2200 nm, preferably from 1900 nm to 2100 nm, and even more preferred approximately 2100 nm, or, from 2800 nm to 3000 nm, and even more preferred approximately 2930 nm, or wavelengths equal to or greater than 4500 nm, such as wavelengths in the range from 4500 nm to 11000 nm, preferably from 4500 nm to 5500 nm, alternatively from 10000 nm to 11000 nm, such as around 10600 nm.

The apparatus according to the invention may not only be used for ablating a thin epidermal layer of the derma of a patient. Also marks on the tissue such as marks from chloasma, liver spots, red spots, tattoos, blood vessels just below the surface, etc., as well as warts, wounds, hair follicles, etc. may be ablated or treated, and hereafter the terms tissue and resurfacing will include these marks and treatments thereof.

It is preferred, that the light source utilized in the present invention is a laser, but also other light sources, such as light emitting diodes and halogen bulbs, may be utilized.

The laser may be any laser capable of emitting light with sufficient power for illuminated cells to vaporize, such as $CO_2$ lasers, YAG lasers, such as Erbium YAG lasers, Holmium YAG lasers, Nd YAG lasers, etc., semi conductor lasers, pulsed lasers, gas lasers, solid state lasers, Hg lasers, excimer lasers, etc.

Present $CO_2$ lasers emit light at a wavelength of 10600 nm. The $CO_2$ laser is particularly well suited as a light source in an apparatus for ablating dermal cells as water has a high energy absorbance at 10600 nm and the $CO_2$ laser is capable of reliably delivering the required laser power.

Erbium YAG lasers emit light at a wavelength of 2930 nm. Water absorbs less energy at this wavelength that at 10600 nm. Therefore, the Erbium YAG laser may be preferred for ablating thinner layers of dermal cells than may be ablated with a $CO_2$ laser. Tissue having been treated with light emitted from an Erbium YAG laser may heal faster than tissue having been treated with $CO_2$ laser light as a thinner layer of dermal cells is influenced by Erbium YAG laser light. An erbium YAG laser may also be preferred when photocoagulation of blood vessels should be avoided.

A CO laser emits light in the 4500 nm to 5500 nm wavelength range. Water absorption at these wavelengths is somewhat less than water absorption at 10600 nm. A CO laser light source is presently preferred for dental treatment, e.g. for removal of carries, as dentine is not influenced by illumination of light from a CO laser.

A Nd YAG laser with a frequency doubled output beam in the 520–680 nm wavelength range is presently preferred as a light source for treatment of hypervasculation. Light in this wavelength range causes photocoagulation of blood without affecting surrounding tissue provided that an appropriate intensity of the light beam is directed towards the micro vessels for an appropriate period of time. Coagulation stops blood flow in the treated vessels whereby discoloration of the skin also stops.

Typically, a power density greater than about 50 W/mm2, such as a power density in the range from about 50 W/mm2 to about 180 W/mm2, is adequate for vaporizing cells with a minimum of damage to the surrounding tissue.

However, when removing hairs, the wavelength of the light is preferred to be approx. 800 nm. At this wavelength the absorbtion of the light in the hair follicles is lower than at higher wavelengths, and the power density must therefore be higher than 180 W/mm2, preferable higher than 300 W/mm2. Generally, the power density is adapted to the wavelength and the tissue to be treated.

The optical fiber for interconnection of a light source with a handpiece according to the present invention may be any fiber, such as a poly-crystalline silver halide fiber, etc, that is suitable for transmission of light emitted from the light source and that is made of a material that allows repeated bending of the fiber, so that an operator can freely manipulate the handpiece in order to direct the light beam toward various areas of a patient.

It is preferred to shape the handpiece ergonomically so that a comfortable hand grip is provided for the operator of the apparatus. For example, it is preferred to direct the light beam towards a target area at a substantially right angle to the area. The ergonomic form of the handpiece allows the operator to point the light beam at a substantially right angle to the target surface without having to bend the wrist in an uncomfortable way.

Preferably, the handpiece is light so that it is easy for the operator to hold the handpiece and bring it into any desired position in relation target surface to be treated. The weight of a preferred handpiece according to the present invention—cables and fibers not included—is less than 300 grams, such as 290 grams, or such as 250 grams.

User interface means may be provided for selection of parameters relating to the operation of the handpiece, positioned on the housing of the handpiece.

The parameters may comprise traversing velocity of the output light beam from the handpiece, intensity of the output light beam emitted form the handpiece, size of the target surface area to be traversed by the output light beam, shape of the target surface area to be traversed by the output light beam, etc.

The user interface means may comprise a first button, e.g. a membrane switch, for selection of a parameter type by stepping through a set of parameter types, such as the set listed above or any subset thereof.

The user interface means may further comprise a second button, e.g. a membrane switch, for selection of a parameter value of the parameter type currently selected by stepping through a corresponding set of parameter values.

A set of light emitting diodes may be provided for indication of the set of currently selected parameter values.

It is an important advantage of provision of the user interface at the handpiece that an operator of the handpiece is able to simultaneously select operational parameters of the handpiece and observe resulting changes in treatment effects as the operator is not forced to shift his field of view from the surface area to be treated to a user interface panel positioned somewhere else, e.g. behind the operator.

Preferably, the buttons are positioned on the housing of the handpiece so that single-handed operation is possible, preferably, with the right as well as with the left hand.

The user interface means may further comprise a foot pedal. The output beam traverses a target surface area when the operator depresses the pedal. Preferably, output beam traversing is stopped immediately when the operator releases the pedal.

The deflecting means may comprise any optical component or components suitable for deflecting light of the wavelength in question, such as mirrors, prisms, grids, diffractive optical elements, such as holograms, etc, etc.

The deflecting means are preferably movably mounted for displacement of the deflecting means as a function of time, so that the light beam emitted from the handpiece may traverse a surface along a desired curve while the handpiece is kept in a fixed position. Preferably, the deflecting means are rotatably mounted, and the actual deflection of the light beam is determined by the current angular position of the deflecting means.

Moving means may be utilized to control positions of the deflecting means, such as actuators, such as piezo electric crystals, the displacement of which is controlled by applying a specific electric voltage to their electrodes, electro motors generating linear or rotational displacements, galvanometers, magnetically activated or controlled actuators, pneumatic actuators, hydraulic actuators, etc.

The positions of the deflecting means may be controlled by deflecting control means adapted to control the moving means so that the deflecting means deflect the light beam in such a way that it traverses a target surface along a desired curve.

According to a preferred embodiment of the invention, a handpiece is provided, having two mirrors that are rotatably mounted in the path of the light beam in the handpiece. The rotational axis of the mirrors may be substantially perpendicular to each other in order to obtain two dimensional deflection of the light beam.

Alternatively, the movable deflecting means may comprise one mirror that is rotatable around two axes that may be substantially perpendicular to each other.

The moving means for the mirrors may be constituted by electro motors, e.g. each mirror may be directly connected to a shaft of a corresponding motor, whereby each motor is used for angular positioning of the corresponding mirror.

In order to minimize the size of the handpiece, it is preferred to mount the motors with their respective shafts in a common plane. For example, one motor may be a linear motor, such as a linear step motor, generating linear displacements. The shaft of this motor may be connected to the mirror at a first edge of the mirror, while a second and opposite edge of the mirror is rotatably connected to the handpiece. By pushing or pulling the first edge by the linear motor, the mirror is rotated about its rotational axis. The other motor, preferably a galvanometer, may be connected to the other mirror in the conventional way described above, whereby the two mirrors may be rotated around substantially perpendicular axes.

The deflecting control means may be adapted to control the moving means so that the desired curve is a substantially straight line.

Preferably, the deflecting control means are adapted to control the moving means so that the light beam traverses a target surface area line by line.

It is an important advantage of the line by line traversing pattern that areas of any arbitrary shape, such as polygonal, such as rectangular, quadratic, triangular, etc, or circular, elliptic, etc, may be traversed line by line by appropriately controlling the starting point and stopping point of light emission along each line traversed.

Preferably, the first deflecting control means are adapted to control the first moving means so that the lines are traversed sequentially i.e. neighbouring lines are traversed successively. This minimizes the requirement for the operator to be able to keep the handpiece steady in a desired position because when lines are traversed successively, neighbouring lines are traversed within a very short time period so that involuntary hand movements of the operator does not lead to traversing overlap i.e. involuntary hand movements can not within the very short time period during which a single line is traversed move the handpiece back to the line previously traversed which would lead to uneven treatment of the target surface.

If an interlacing traversing pattern were utilized, i.e. every second line of the target surface area is traversed and after that the remaining lines inbetween are traversed, there would be sufficient time between traversing of neighbouring lines to allow involuntary movements of the handpiece to a line previously traversed leading to repeated treatment of one area that may damage tissue at that area and leaving another area without treatment.

Thus, according to a third aspect of the invention, a method is provided of traversing a light beam across an area of at issue, comprising the steps of emitting the light beam to wards the tissue area, deflecting the light beam with movable deflecting means so that the tissue is traversed by the light beam line by line sequentially, each line being traversed in the same direction.

The first deflecting control means may be adapted to control the first moving means so that the lines are traversed in the same direction whereby substantially the same amount of power per area is delivered uniformly across the target surface area leading to substantially the same temperature increase at any point of the target surface area after traversing.

When a target area is traversed line by line, it is preferred that movement of one mirror causes the light beam to traverse a line while movement of the other mirror moves the light beam to the next line. In the example above, the galvanometer preferably generates the line traversing as the galvanometer can move the mirror at a high speed, and the linear motor preferably generates the displacement of the light beam to the next line to be traversed.

As mentioned earlier, it is preferred to control the amount of energy delivered to cells to be ablated, as the amount of energy must be sufficient for the dermal cells to vaporize and, simultaneously, the amount of residual energy heating non-ablated cells must be so low that non-ablated cells will not be seriously damaged. Thus, when an area of tissue is traversed, e.g. line by line, it is preferred that neighbouring lines substantially abut each other. Clinical investigations have shown that, typically, an overlap of 0.1 to 0.2 mm is acceptable, and a distance between traversed lines of up to 0.1–10.2 mm is acceptable.

In order to control positioning of curves on the target area this accurately, it is preferred to position the movable deflecting means extremely accurately in the handpiece. In the preferred embodiment of the invention, this is accomplished by utilisation of printed circuit technology providing high accuracies of hole positioning of 0.05 mm. The mirrors are rotated around shafts that are mounted in printed circuit boards providing the required positioning accuracy. Further, the motors rotating the mirrors are also mounted on the printed circuit boards providing electrical connections to the motors and the mechanical support and positioning needed.

When traversing a target surface area line by line, it is preferred to traverse each line in the same direction ensuring uniform heating of cells across the target surface area. Further, it is preferred to provide light switching means for preventing emission of the light beam and light switching control means for controlling the light switching means for turning off the light beam, e.g. by switching off the light source, by inserting a light obstructing member in the light path of the beam, etc, while the light beam is moved from the end of a line having been traversed to the start of the next line to be traversed, in order to avoid repeated illumination of areas of the two lines.

Instead of turning the light source off, the light beam may be moved at a speed significantly larger than the traversing speed, during movement from the end of a line to the start of the next line.

Typically, the intensity within the beam of a light beam as generated by the light source varies as a normal function of the distance from the centre of the beam. The optical fiber may be designed or selected to be dispersive in such a way that the intensity function of the light beam emitted from the fiber as a function of the distance to the centre of the beam is substantially rectangular, i.e. the intensity of the beam leaving the fiber decays more slowly towards the edge of the beam than the intensity of a beam as generated by the light source whereby heat is more uniformly generated in cells across a traversed line of tissue.

By pulse width modulating the light source, energy delivered to the target surface may be varied along a traversed line. A fade-in area may be created by starting traversing of each traversed line with short pulses of light between longer periods of no light. As the line is traversed, the duration of the light pulses may be increased while the periods with no light may be decreased. Outside the fade-in area, the light beam may not be pulsed whereby the remaining part of each line is traversed with a constant intensity of the light beam.

Likewise, a fade-out area may be created by after having traversed a part of a line with constant light intensity, pulse width modulating the light source to transmit shorter and shorter pulses of light towards the line at the target surface area ending with no light transmitted at the end of the line.

The fade-in or fade-out traversing patterns may also be created by gradually increasing or decreasing, respectively, the power of the light source, or by decreasing or increasing, respectively, the traversing speed of the light beam.

Alternatively, a combination of these methods may be used.

The shape of the traversed area including the fading area may for example be polygonal, such as rectangular, quadratic, triangular, etc, circular, elliptic, etc.

A traversed line with fade-in and/or fade-out provides a smooth transition from a non-ablated area of tissue to an ablated area of tissue. This is a particularly advantageous feature when the handpiece according to the present invention is used for treatment of small marks on the tissue such as marks from chloasma, liver spots, red spots, tattoos, blood vessels etc.

Light intensity control means may be provided for generating a control signal for transmission to a light source interconnected with the optical fiber and controlling intensity of light emitted by the light source and transmitted through the optical fiber.

The fade-in and fade-out may be provided by controlling the intensity of the light beam and/or the velocity of the traversing light beam along a desired curve and the light intensity control means and/or the deflecting control means may be adapted to provide fade-in and fade-out.

The light intensity control means and/or the deflecting control means may be adapted to control the intensity of the light beam and/or the velocity of the traversing light beam along a desired curve as a function of the position of the light beam inside the area of the target surface area.

To provide the normal ablating of tissue, the light intensity control means may be adapted to provide a substantially constant intensity of the light beam and the deflecting control means may be adapted to provide a substantially constant velocity of the traversing light beam when the traversing light beam is inside a first part of the target surface area.

Keeping the intensity of the light beam substantially at the constant level as provided inside the first part of the target tissue, fade-in and fade-out may be provided by traversing the light beam with a velocity larger than the substantially constant traversing velocity within the first part of the target tissue area.

Likewise, keeping the velocity of the traversing light beam substantially constant inside the first part of the target tissue, the fade-in and fade-out may be provided by emitting a light beam with a smaller intensity than the substantially constant intensity of light emitted within the first part of the target tissue area.

The light intensity control means and/or the deflecting control means may be adapted to provide a varying intensity of the light beam outside the first part of the target surface area. The intensity of the light beam may be varied between a first intensity being substantially identical to the substantially constant intensity in the first part of the target tissue area and zero intensity, i.e. no light is emitted from the output of the handpiece.

The user interface means may also enable selection of parameters relating to fade-in and fade-out, such as traversing velocity of the output light beam from the handpiece in the fade-in or the fade-out area, intensity of the output light beam emitted form the handpiece in the fade-in or the fade-out area, size of fade-in or fade-out areas, shape of fade-in or fade-out areas, etc.

The handpiece according to the present invention may comprise means for controlling the energy-per-area of the light beam along a desired curve on a target tissue area to be resurfaced. In order to obtain the best results when ablating tissue, the energy-per-area of the light beam inside the first part of the target tissue area, should be kept at a substantially constant level.

In order to provide fade-in or fade-out, the energy-per-area of the light beam when outside the first part of the target tissue area may depend on the distance to the first part of the target tissue area, and it is preferred that the energy-per-area of the light beam increases with decreasing distance to the first part of the target tissue area.

In the case where the light beam is invisible, i.e. the wavelength of the light beam is e.g. in the infra red or ultra violet range, a light source generating visible light may be provided for generating a visible light beam that is used to assist the operator by indicating areas towards which the invisible light is directed during traversing. For example, the input connector of the handpiece may be further adapted to connect a second beam-outlet end of a second optical fiber for transmission of a visible light beam to the handpiece. The second optical fiber is aligned in the connector along the desired path of the visible light beam. The handpiece may further comprise movable second deflecting means for deflection of the visible light beam in such a way that the invisible light beam and the visible light beams emitted from the output of the handpiece illuminate substantially the same area of a target surface.

Further, two crossing visible light beams may be emitted from the handpiece, the cross point of the beams indicating the focus point of the invisible light beam.

Preferably, common moving deflecting means are utilised for deflection of all light beams emitted from the handpiece. Zinc selenide lenses may be utilized, as they are transparent for visible light as well as for infra-red light.

In order to further assist the operator of the apparatus, the visible light beam may, e.g. between traversing with the invisible light beam, be traversed around at least a part of the circumference of the target surface area thereby indicating the size, shape and position of the target surface area to be traversed with the invisible light beam.

When a polygonal shape of the target surface area has been selected, the visible light beam may, e.g. between traversing by the invisible light beam, be traversed along one edge of the polygon.

Thus, the method may further comprise the step of transmitting a visible light beam towards the target surface area utilizing the movable deflecting means.

The method may further comprise the step of traversing the visible light beam along at least a part of the circumference of the target surface area to be traversed by the invisible light beam.

When the shape of the tissue area traversed is polygonal, the method may comprise traversing the visible light beam along one edge of the polygon to be traversed by the invisible light beam.

In order to assist the operator of the apparatus in keeping a constant distance from the output of the handpiece to the surface of the tissue to be ablated, the handpiece may comprise a distance member connected to the handpiece at the output with fastening means.

As the distance member will touch the patient, it is desirable to insert a new, disinfected member before treatment of a new patient and thus, it is preferred that the fastening means comprises a magnet so that a used distance member can easily be disconnected from the handpiece, e.g. for autoclaving, and so that a new member can easily be connected to the handpiece.

The handpiece according to the present invention may further comprise a processor for control of the handpiece and comprising one or more control means, such as deflecting control means, light switching control means, means for controlling the light intensity control means, etc. The processor may further be connected to the user interface means and may be adapted to control the functions of the handpiece in accordance with the user interface selections.

Thus, the processor may be adapted to control energy density received by the target surface when traversed by the invisible light beam.

Further, the processor may be adapted to control energy density received by the target surface at a specific position as a function of the position along a desired curve traversed by the invisible light beam e.g. in order to provide fade-in and fade-out.

The processor may comprise a memory, such as an EEPROM, for storing of different parameters of traversing patterns and fade-in and fade-out patterns, such as target surface area size, traversing duration, etc.

The handpiece may further be provided with a computer interface facilitating reception of traversing pattern parameters generated in a computer and transmitted to the handpiece for storage in the memory. The user interface may utilized for selection of a specific traversing pattern from the set of patterns stored in the memory as previously described. The computer may be any programmable electronic device capable of storing, retrieving and processing data, such as a PC.

It is an important advantage of provision of a processor in the handpiece that signal lines between the handpiece and an external device controlling the handpiece are not needed. This reduces weight of the handpiece with cables connected. Further, electrical noise on control lines is minimized because of reduced lengths of the lines. Still further, control speed is increased as capacitance of a short line is small.

Various traversing patterns may be created on a PC and be downloaded to the memory of the handpiece. The patterns may stored in the form of a table of parameters defining number of lines, length of lines, distance between lines, start and end points of fade-in and fade-out of each line, points of turn on and turn off of the traversing light beam, etc of each traversing pattern stored.

A traversing pattern box may be provided, containing a processor, a memory and interface means for storage of traversing patterns generated, e.g. on a PC and transmitted to the box through the interface means for storage in the memory. The interface means of the box and the computer interface of a handpiece may be interconnected and the various traversing patterns stored in the box may be transferred to the memory of the handpiece whereby traversing patterns created at a single PC may be distributed to a plurality of handpieces that may be situated remotely from the PC.

According to a fourth aspect of the invention, a cable i is provided, comprising an optical fiber for transmission of light through the fiber and positioned at the centre of the cable, a teflon tube for protection of the fiber against influence from the environment, the fiber being positioned within the teflon tube, a plastic tube for protection of the teflon tube and the fiber against mechanical stress, the teflon tube being positioned within the plastic tube, a wire for protection of the cable against tensions and overloads that is positioned next to the plastic tube, and a spiral tube for holding the optical fiber, the teflon tube, the plastic tube and the wire none of which are fixed in position relative to each other in the spiral tube but are allowed to move in relation to each other when the cable is bended whereby a very flexible cable is provided.

The cable may further comprise a second optical fiber positioned within the spiral tube next to the teflon tube for transmission of visible light.

BRIEF DESCRIPTION OF THE DRAWINGS

In the following, a preferred embodiment of a tissue treatment apparatus will be described with reference to the drawings, wherein.

DETAILED DESCRIPTION OF THE DRAWINGS

Figure 1:
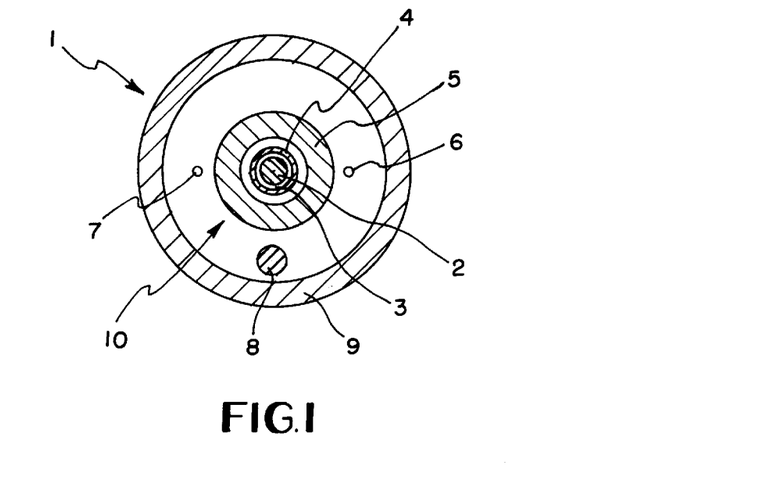
FIG. 1 shows a cross section of a cable for transmission of light from a laser source to the handpiece according to the invention.

FIG. 1 shows a cross section of a cable 1 for transmission of light from a laser source to the handpiece of an apparatus for tissue treatment. An optical fiber 2 is positioned at the centre of the cable 1. The optical fiber 2 is made of silver chloride and silver bromide (silver halide), which is especially designed for transmission of light at a wavelength of app. 10.6 $\mu$m. The optical fiber 2 is covered by a cladding 3, also made of silver bromide and silver chloride but mixed in another ratio, which prevents the light travelling in the fiber 2 to escape from the fiber 2. The diameter of the fiber 2 is app. 500 $\mu$m, while the cladding 3 is app. 50 $\mu$m thick. The fiber 2 and the cladding 3 are protected against influence from the environment by a teflon tube 4. The fiber 2 and the cladding 3 are also protected against mechanical stress by a plastic tube 5 also protecting the teflon tube 4. The fiber 2, the cladding 3, the teflon tube 4 and the plastic tube 5 can be considered to constitute an optical fiber unit 10. Included in the cable 1 are two glass fibers 6, 7 and a wire 8. The two glass fibers 6, 7 are specially designed optical fibres designed with a small NA (numerical aperture) designed for visible light at a wavelength of app. 650 nm. The wire 8 is provided for protecting the cable 1 against tensions and overloads. The optical fiber unit 10, the two glass fibers 6, 7, and the wire 8 are surrounded by a spiral tube 9 made of stainless steel. The optical fiber unit 10, the two glass fibers 6, 7, and the wire 8 are not fixed in position relative to each other inside the spiral tube 9, but can move in relation to each other. This makes the cable 1 very flexible when it is moved, and it provides at the same time a good protection of the fragile fibers 2, 6, 7. Inside the spiral tube 9 and along the optical fiber unit 10, the two glass fibers 6, 7, and the wire 8, compressed air is blown. The air is blown out in front of the optics, blowing away any ablated material that otherwise could deposit on the optics.

The light beam from a CO2 laser is coupled into the optical fiber 2 at one end of the fiber 2 positioned at one end of the cable 1. At the same end of the cable 1, light beams from two diode lasers are coupled into the glass fibers 6, 7, respectively. The light beams are transmitted in the respective fibers from the inlet end to the outlet end, which is connected to a handpiece.

Figure 2:
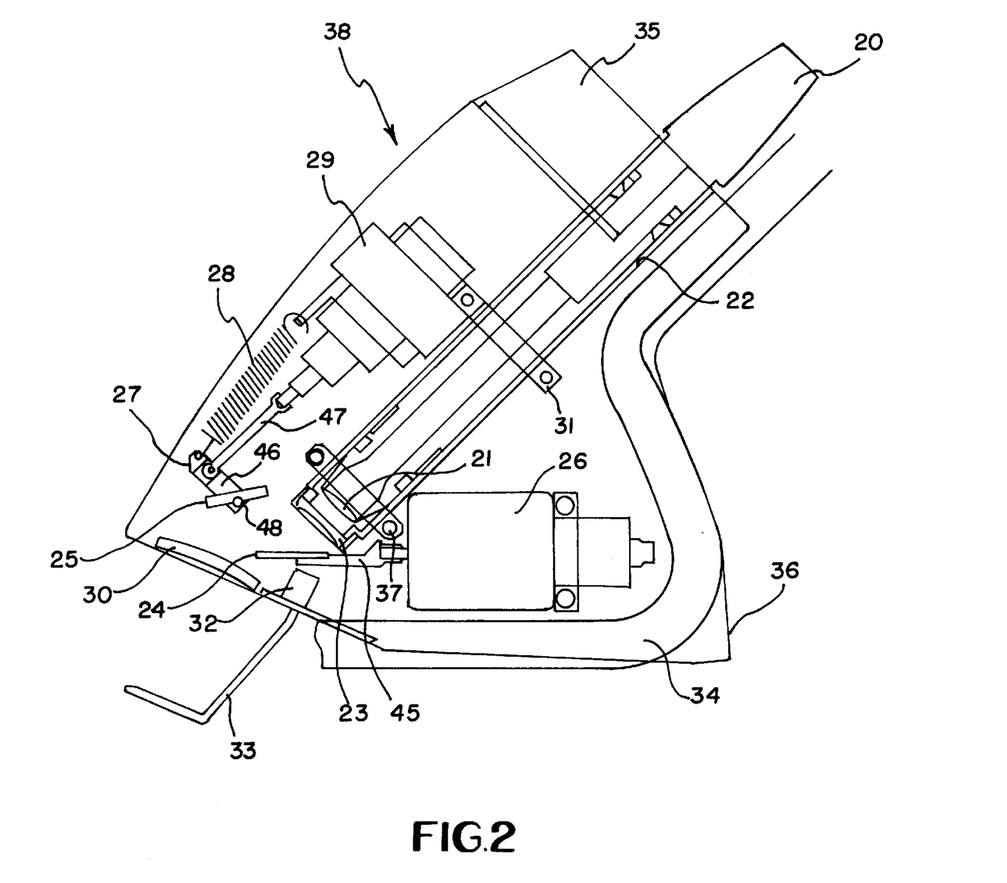
FIG. 2 shows a cross section of a handpiece according to the present invention.

FIG. 2 shows a handpiece 38 according to the present invention. The cable 1 (not shown in FIG. 2) is connected to the handpiece 38 at a fiber inlet part 20, and guided through a tube 22 which is held in place in the handpiece 38 by the holding means 31 and 37. The fiber inlet part 20 also serves as a cable protecting sleeve. The light beams transmitted in the optical fiber 2 and the two glass fibers 6, 7 are radiated from the outlet ends of the fibers 2, 6, 7, through a lens system 39—shown in greater detail in FIG. 3—to an object, e.g. a human tissue surface. The outlet ends of the fibers 2, 6, 7 are positioned at the holding means 37 at a distance appropriate for the focusing lens 21 to focus the light from the fibers 2, 6, 7 on the object.

Figure 3:
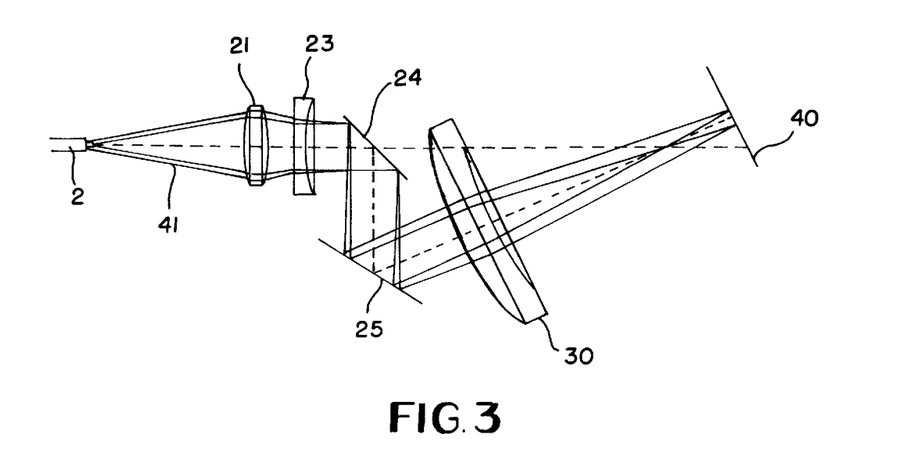
FIG. 3 shows the lens system of the handpiece shown in FIG. 2 in greater detail.

In FIG. 3, the lens system is shown in greater detail. The light beams radiated from the outlet end of the fibers 2, 6, 7, are focused by the first focusing lens 21 and collimated by the collimating lens 23. The collimated light beam is transmitted from the collimation lens 23 via a first mirror 24 and a second mirror 25 to a second focusing lens 30 which focuses the light beams on the object 40, which e.g. can be the facial tissue of a human being. The distance between the focusing lens 30 and the focus plane at the object 40 is preferably approx. 27 mm.

The movable first deflecting means also constitute the second movable deflecting means and comprise the first mirror 24 that is mounted on the first moving means that also constitute the second moving means and comprise a galvanometer 26 with an indicator 45 and positioned in the handpiece 38 of the handpiece according to the invention. When an electric current is driven through the coil of the galvanometer 26, the magnetic field generated by the current will make the indicator rotate around a longitudinal axis of the indicator 45. The first mirror 24 will thereby be rotated, and the second light beam will be deflected at an angle twice the angle rotated by the mirror 24 in relation to the first light beam. The positioning resolution of the galvanometer 26 is limited by the electronic deflecting control means controlling the galvanometer 26 to 255 positions.

The movable first deflecting means also comprise the second mirror 25 is mounted on an arm 46 actuated by a linear actuator 29 comprised by the first moving means. When the linear actuator 29 activates the actuator arm 47, the arm 46, and thereby the second mirror 25, is rotated around the shaft 48. A spring 28 is connected to one end of the arm 46 and to a non-moving part of the linear actuator 29 in the other end so as to neutralize wobble that may be present in the shaft 48. When the second mirror 25 is rotated around the shaft 48, the light incident on the second mirror 25 is deflected in an angle twice the angle rotated by the mirror 25. The linear actuator 29 may be controlled by applying a sequence of pulses across the terminals (not shown) of the actuator 29. The positioning resolution of the linear actuator is discrete and limited to a maximum number of steps of approx. 200.

The optics of the apparatus limits the possible scan area to approx. 10 * 10 mm, corresponding to an angular displacement of the mirror 24 of approx. ±8° and an angular displacement of the mirror 25 of approx. ±5°, even though the maximum movement of the mirror 24 is approx. ±11° and the maximum movement of the mirror 25 is approx. ±10°. The extra possible movement which is not used during scanning is used during start-up of the system to ensure accurate and reliable speed before the treatment scan is started.

By controlling the current to the coil of the galvanometer 26 and the pulse sequence applied across the terminals of the linear actuator 29, the direction of light beams sent through the focusing lens 30 towards the object 40 can be controlled. It is thus possible to create different kinds of scan patterns of the light beam, such as rectangular or circular scan patterns.

The optics and electronics of the handpiece 38 are protected by a plastic housing 36 provided in an ergonomical shape. An air tube 34 may be positioned on the handpiece 38 for providing suction of air from in front of the optics of the handpiece 38 in order to absorb any material ablated from the tissue of the object being treated with the apparatus of the present invention.

The light beams from the two glass fibers 6, 7 transmitted from the cable 1 through the optics of the handpiece and to the object, intersects at a distance equal to the focal length of the focusing lens 30, i.e. at the distance where the light from the CO2 laser is focused. This is the distance at which the handpiece should be held from the object to get the best treatment result, and the intersection of the two visible light beams helps the operator keeping the correct distance to the tissue surface.

Because of the importance of keeping the CO2 focal point on the tissue surface, the presently preferred embodiment of the handpiece 38 further comprises a magnetic distance member 33 connected to the handpiece 38 with a magnet. As the distance member 33 is magnetic, it is easy to connect to and disconnect from the handpiece 38.

Figure 4:
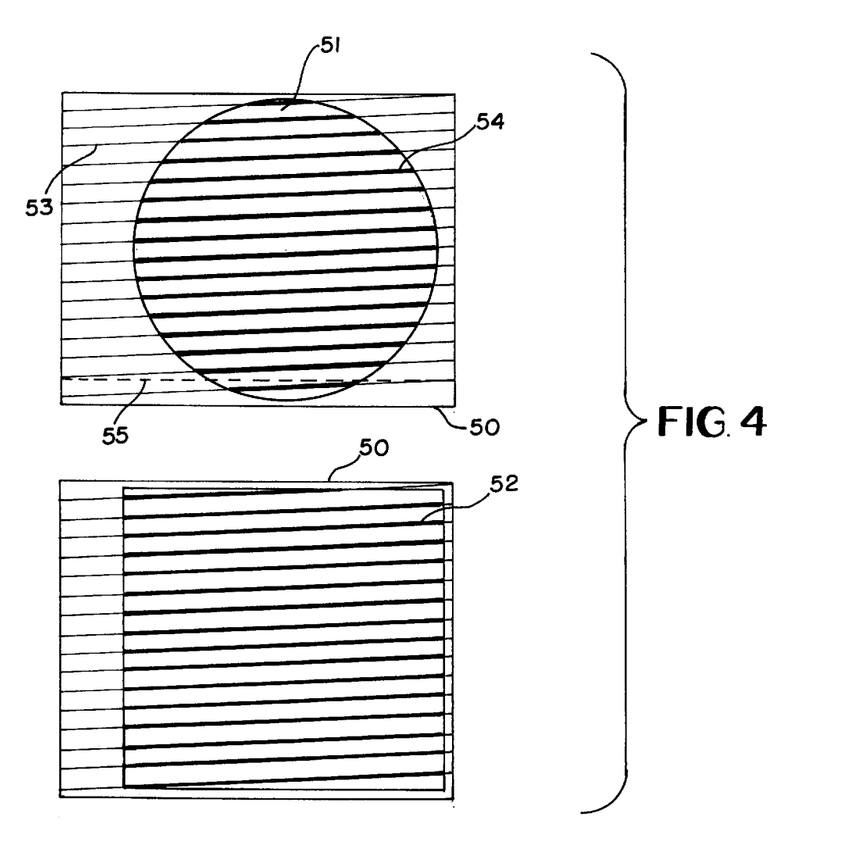
FIG. 4 shows a circular and a quadratic scan area.

In FIG. 4, a quadratic scan area 52 and a circular scan area 51 are shown. The actual laser scan area is indicated by reference numeral 50, but only the scan areas 51, 52 are used for tissue treatment. The thin lines 53 and the thick lines 54 indicate the path which the laser beam follows during a scan.

The thin lines 53 indicate parts of the scan where the laser is turned off, while the thick lines 54 indicate parts of the scan where the laser is turned on.

The scan is performed as a slow forward/fast return-scan (a TV-scan, but without interlacing). The scan starts at the lower left corner of the actual scan area 50. The laser beam is moved towards the right, and when the laser beam enters the tissue treatment scan area 51 or 52, the laser is turned on. When the laser beam leaves the tissue treatment scan area 51 or 52, the laser is turned off, and when the laser beam reaches the right edge of the actual scan area 59, the beam is quickly retraced or moved to the left edge of the actual scan area 50, and a new scan line can be initiated.

In stead of turning the laser on and off, the speed of the movement of the laser beam may be increased to a speed sufficiently high for the laser beam not to ablate the tissue surface.

The fast movement (trace and retrace) of the laser beam between the right and left edges of the actual scan area 50, is accomplished by controlling the galvanometer 26. In order to let the mirror 24 settle after the fast movement from the right edge of the actual scan area 50 to the left edge, the first part of the scan line is not used for tissue treatment. The slower movement of the laser beam from the bottom to the top of the actual scan area 50 is accomplished by controlling the linear actuator 29 in a constant movement of the mirror 25.

A quadratic scan area of approx. 9*9 mm comprises 30 scan lines, and the max. scanning speed is app. 300 mm/s.

The operator of the apparatus controls the scanning using a pedal. When the pedal is activated, a scanning starts. After finishing the scanning, the CO2 laser is turned off, and the visible light beam scans around at least a part of the circumference of the scan area 51 or 52 thereby indicating the size, shape and position of the scanned area 51 or 52. The operator may now move the handpiece and select a new scan area, e.g. a scan area abutting the area just scanned, and when the operator releases the pedal and again activates it, a new scanning will take place. In this way, the operator of the apparatus may easily scan larger areas of the tissue by scanning several neighbouring areas.

Figure 5:
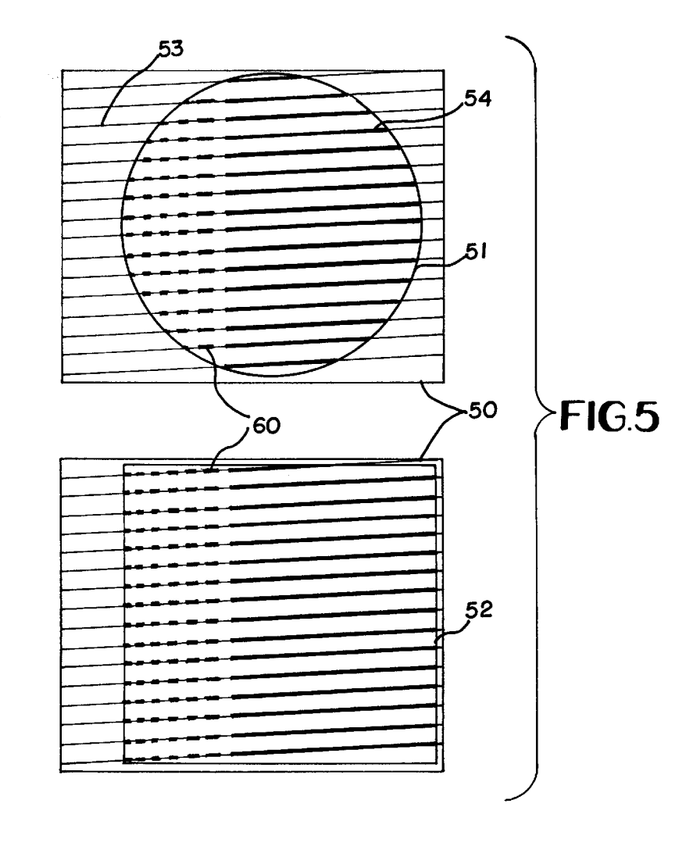
FIG. 5 shows a circular and a quadratic scan area with a single-sided fade-out scan pattern.

In FIG. 5, a quadratic scan area 52 and a circular scan area 51 with single-sided fade-out intensity scan lines 60 are shown. The fade-out intensity is accomplished by pulse modulating the laser power in shorter pulses as the intensity is faded out.

Figure 6:
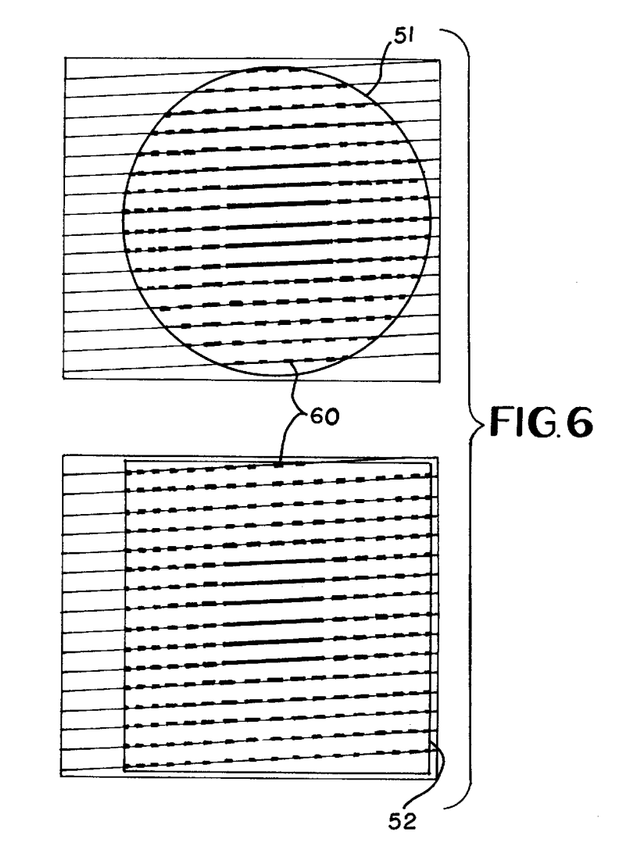
FIG. 6 shows a circular and a quadratic scan area with a four-sided fade-out scan pattern.

In FIG. 6, a quadratic scan area 52 and a circular scan area 51 with four-sided fade-out intensity scan lines 60 are shown.

The effect of using the fade-out intensity scan lines 60 is to create a smooth transition from a non-ablated area of the tissue to an ablated area.

The size and shape of the fade-in and fade-out scan areas may be selected using selectors on the handpiece 38.

It should be understood that a fade-in or a fade-out effect may be accomplished by gradually increasing or decreasing the intensity of the laser light, respectively, or by decreasing or increasing the speed of the movement of the laser beam, respectively.

Figure 7A:
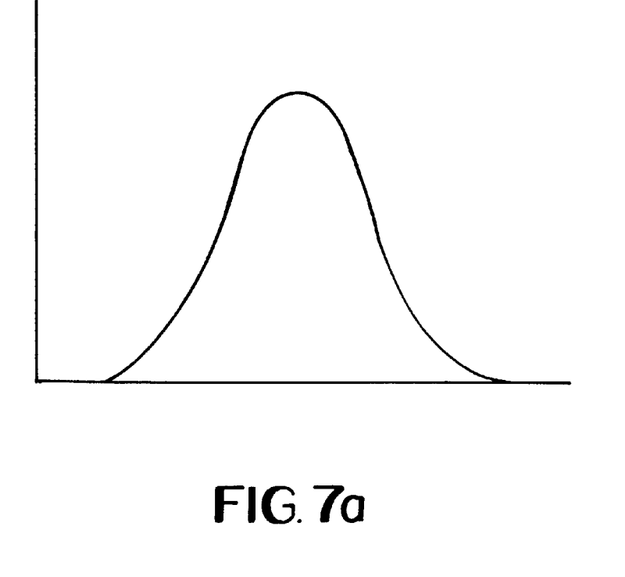
FIG. 7 shows a cross section of a standard laser beam and an example of a cross section of a laser beam more suitable for use in the handpiece of the present invention.

In FIG. 7a, the beam profile for a standard laser beam transmitted via mirrors and standard lenses is shown. The beam profile is Gaussian with a high light intensity in the center of the beam. Only the high intensity center of the beam can ablate the tissue.

Figure 7B:
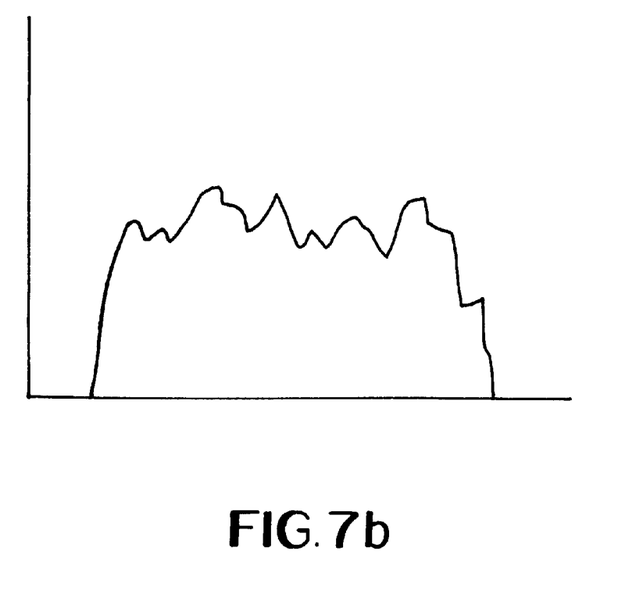

In FIG. 7b, a typical beam profile for a laser beam transmitted through the optical fiber 2 used in the apparatus according to the present invention is shown. The high intensity part of the beam profile is not limited to the center of the profile, but almost the complete beam profile has a sufficiently high intensity for ablating the tissue. When the laser light at 10.6 $\mu$m wavelength is transmitted through the 500 $\mu$m optical fiber 2, the laser light is changed from a single mode laser beam to a multi mode laser beam. A multi mode laser beam has a more uniform intensity profile compared to the single mode laser beam.

When using a Gaussian shaped beam, there is a risk of overexposing the tissue exposed by the center of the beam, while the parts of the tissue exposed by the edges of the beam are underexposed. This may result in thin lines of scars in the tissue. Using a non-gaussian shaped beam, as the beam provided by the optical fiber used in the apparatus according to the present invention, the risk of making scars in the tissue is minimized.

One of the advantages of using a broadened light beam is, that the risk of drawing lines on the tissue as with the high intensity Gaussian beam is minimized.

Figure 8:
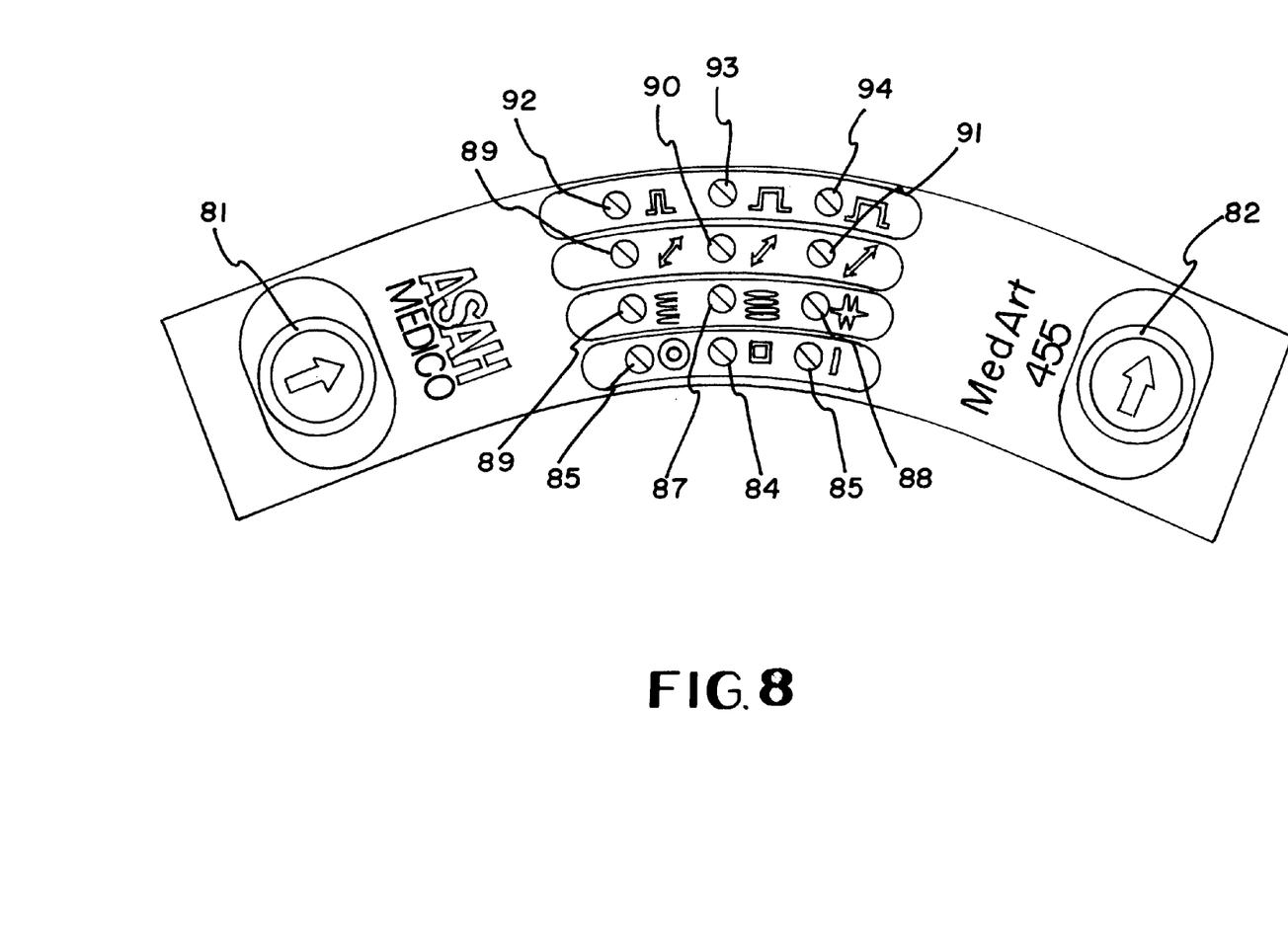
FIG. 8 shows an unfolded view of the user interface means provided at the handpiece.

In FIG. 8 the user interface means of the handpiece is shown unfolded. The user interface means comprise two push buttons 81, 82 and twelve light emitting diodes arranged in four rows, each row comprising three diodes.

Each row is used to indicate selection of a parameter value of a corresponding parameter type.

The row comprising diodes 83, 84, and 85 indicates selection of shape of the scan pattern. Diode 83 is turned on when a circular scan pattern is selected, diode 84 is turned on when a quadratic scan pattern is selected and diode 85 is turned on when a line scan pattern is selected.

The row comprising diodes 86, 87, and 88 indicates selection of fade-in and fade-out patterns. Diode 86 is turned on when a pattern with fade-in from the left is selected, diode 87 is turned on when a pattern with fade-in from the left and fade out to the right is selected, and diode 88 is turned on when a pattern with fade-in and fade-out, respectively, from both sides as well as from top and bottom of the scan pattern is selected.

The row comprising diodes 89, 90, and 91 indicates selection of the size of the scan pattern. The diode 89 is turned on when a small scan pattern is selected, diode 90 is turned on when a medium sized scan pattern is selected, and diode 90 is turned on when a large scan pattern is selected.

If the quadratic scan pattern is selected, the scan area may be approx. 9*9 mm, approx. 6*6 mm, such as 6,5–7 mm * 6,5–7 mm, or approx. 3*3 mm, such as 3,5–4 mm * 3,5–4 mm, if the scan pattern is circular, the diameter of the circle may be approx. 9 mm, such as 10 mm, approx. 6 mm, such as 6,5–7 mm, or approx. 3 mm, such as 3,5–4 mm, and if the scan pattern is a line, the length of the line may be approx. 9 mm, such as 10 mm, approx. 6 mm, such as 6,5–7 mm, or approx. 3 mm, such as 3,5–4 mm.

In the example above, the number of scan lines in a quadratic or circular scan may be approx. 10 scan lines per scan area if the scan size is small, or the number of scan lines may be approx. 20 scan lines per scan area if the scan size is medium, or the number of scan lines may be approx. 30 scan lines per scan area if the scan size is large.

Thus, the time to complete a scan depends on the scan size and the scan speed. If for example the scan speed is high the time to complete a scan is approx. 0,15 sec if the scan size is small, approx. 0,5 sec if the scan size is medium, and approx. 1 sec if the scan size is large. If the scan speed is medium the time to complete a scan is approx. 0,2 sec if the scan size is small, and approx. 0,7 sec if the scan size is medium, and approx. 1,5 sec if the scan size is large. If then the scan speed is slow the time to complete a scan is approx. 0,3 sec if the scan size is small, and approx. 0,9 sec if the scan size is medium, and approx. 2 sec if the scan size is large.

The row comprising diodes 92, 93, and 94 indicates scan velocity. Diode 92 is turned on when a high scan velocity is selected, diode 93 is turned on when a medium scan velocity is selected, and diode 94 is turned on when a low scan velocity is selected.

Depending on the application of the handpiece, the high velocity may be equal to 350 mm/s. At the high velocity approx. 5 J/cm2 is supplied to the scanned area. The medium velocity may be equal to 225 mm/s at which velocity approx. 8 J/cm2 is supplied to the scanned area. The low velocity may be equal to 175 mm/s at which velocity approx. 10 J/cm2 is supplied to the scanned area.

When scanning on different types of tissue, it is preferred to adjust the scan speed of the light beam in stead of adjusting the output power of the light beam. When scanning on tissue with a low absorption of light, such as dry skin, it is preferred to generate a high power density on the tissue, and the scan speed mode should be set to low. When scanning on tissue with an average absorption of light, the scan speed mode should be set to medium, and when scanning on tissue with a high absorbtion of light, the high scan speed mode should be selected.

Depression of the push bottom 82 causes one of the light diodes to start flashing in one row indicating that parameter values of the type corresponding to that row can be selected. By depressing push button 82 once more, a light diode in another row will start flashing and thus, by repeatedly depressing push button 82, parameter values of each type indicated by the user interface means may be selected.

In the row in which a light diode is flashing, the desired parameter value may be selected by depressing the push bottom 81 until the diode indicating selection of the desired parameter value is flashing.

Thus, selection of scan area parameter values of the handpiece may be done immediately prior to scanning of the treatment area. Selection is very simple and does not require utilization of an external computer for programming of desired scan patterns.

The different scan pattern parameter values are stored in the memory of the handpiece. This provides an easy to learn and understand user interface requiring a minimum of teaching of the operator. Furthermore, the weight of the cables and thereby of the handpiece is reduced because there is no need for cables connecting the handpiece to an external controller. Further, by storing scan pattern parameters in the memory of the handpiece, costs for an expensive programming device is avoided. Other scan patterns than the ones described above may be downloaded to the memory of the handpiece through its computer interface. When the desired scan patterns have been downloaded, the computer interface can be disconnected from the scan pattern parameter value source and the handpiece will be ready for use.

All functions of the handpiece is controlled by the processor. The processor is interfaced with the laser unit, the light emitting diodes and the two push buttons of the user interface means.

Figure 9:
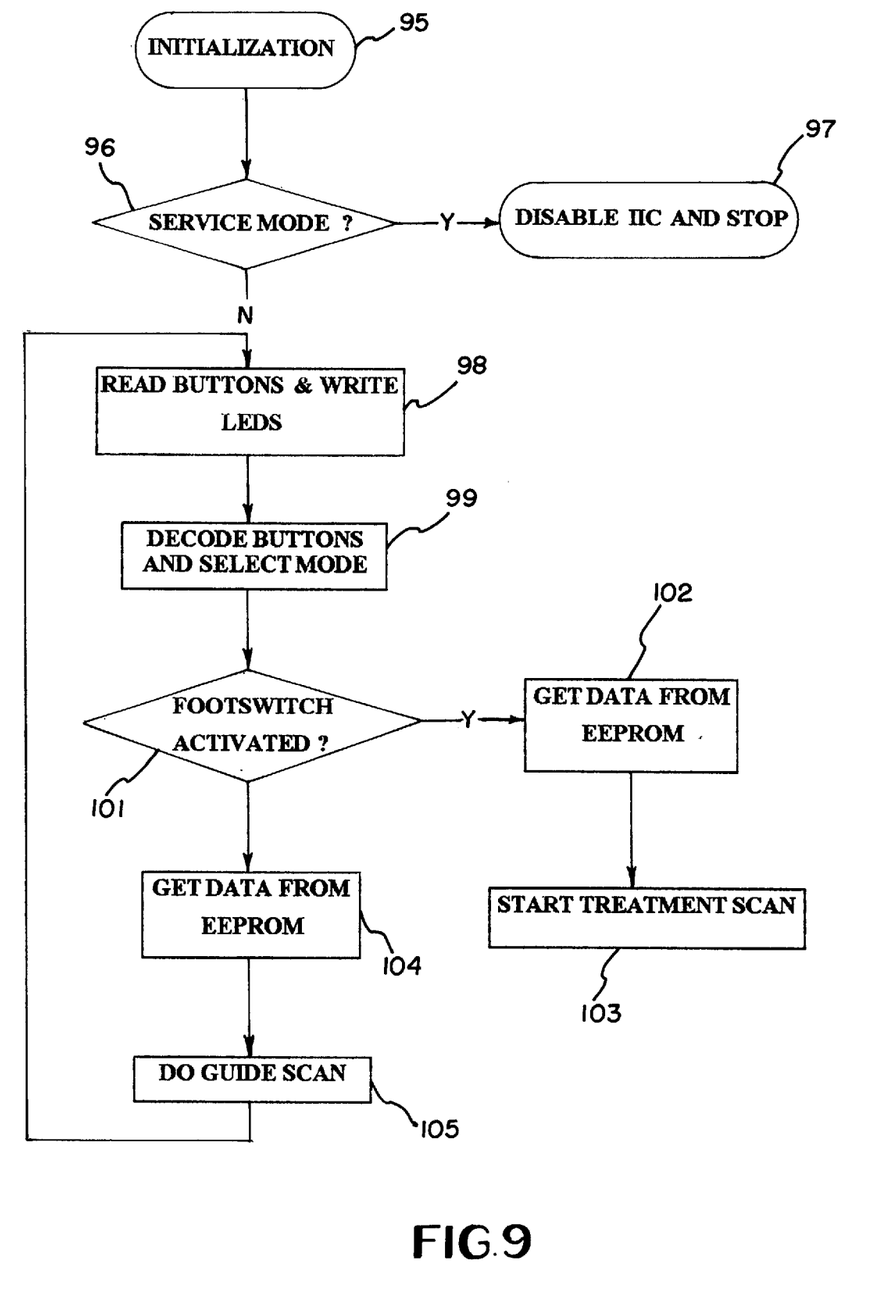
FIG. 9 shows a flow chart of the software controlling the scan parameters.

In FIG. 9 a flow chart illustrates processor operation before the treatment scan is started.

Processor operation starts in step 95 where the processor is initialized. Hereafter in step 96, the processor checks if the handpiece is in a service mode. If so, the bus IIC, which reads and writes the outputs from the two interface integrated circuits IC11 and IC12 is disabled in step 97 as described further in the next section. If not, in step 98 activation of the push buttons of the user interface means are detected and the light emitting diodes are turned on and off accordingly as previously described. In step 99, the parameter value selections are recorded and the corresponding scan pattern is selected. In step 101, the processor checks if the foot pedal is depressed or activated. If so, in step 102 the processor gets data from the EEPROM and starts the treatment scan in step 103. If not, the processor gets data from the EEPROM in step 104 and perform a guide scan in step 105, i.e. the visible light beam traverses the circumference of the scan pattern or a part thereof as previously described. Hereafter the process is repeated from step 98.

When the system is in service mode an external unit may take over the control of the handpiece from the handpiece processor by taking control of the serial IIC bus. The handpiece processor checks whether an external computer is connected to the bus and if so control of the bus is transferred to the external computer. This may be useful when testing and adjusting the handpiece and when reprogramming the scanner.

Figure 10:
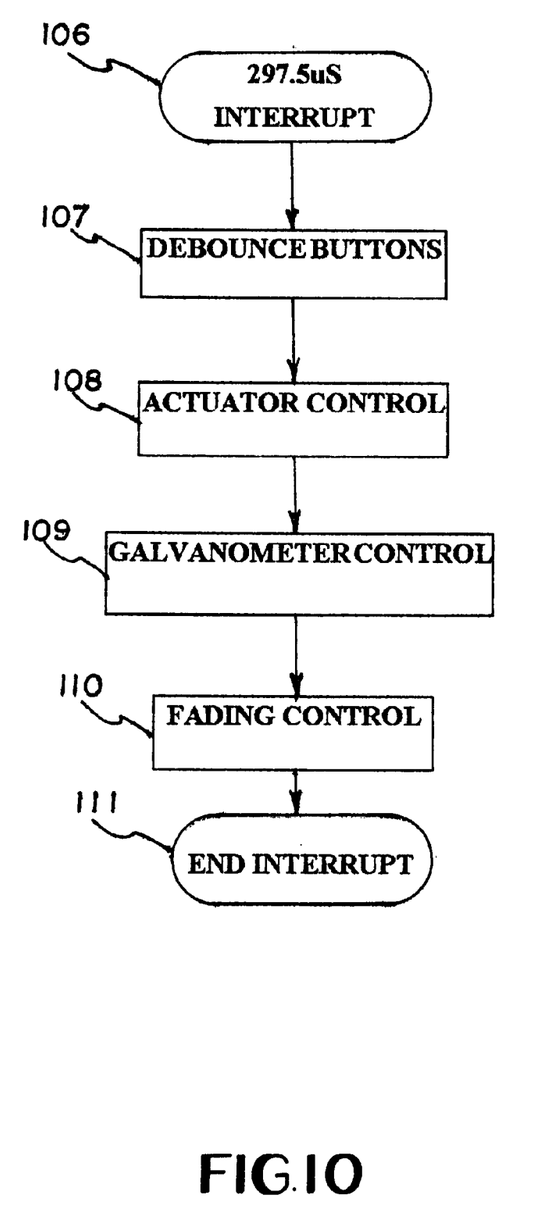
FIG. 10 shows a flow chart of the software controlling the scan parameters.

In FIG. 10 a flow chart illustrates a processor interrupt. This interrupt is executed every 297,5 microseconds and is set up during start up of the scanning sequence, and the set up information comprises information concerning the size, area, intensity, and velocity of the scan. At each interrupt, the processor checks whether one of the push buttons has been activated, and it reads in the table of the EEPROM the next position of the treatment beam and commands the moving means to the next position.

The first step 107 is debounce control of the buttons. Each time a signal from a push button is received, the signal is checked for 20 ms to avoid noise. The buttons are checked during start up and during guide scanning but during treatment scanning only the pedal is checked.

In step 108 the actuator is controlled according the set up information and stepped as required. In step 109, the galvanometer is controlled and the current regulating the movements of the galvanometer is controlled. Further, in step 110 the fading or intensity of the beam is controlled according to the set up information. The interrupt is ended in step 111.

Figure 11:
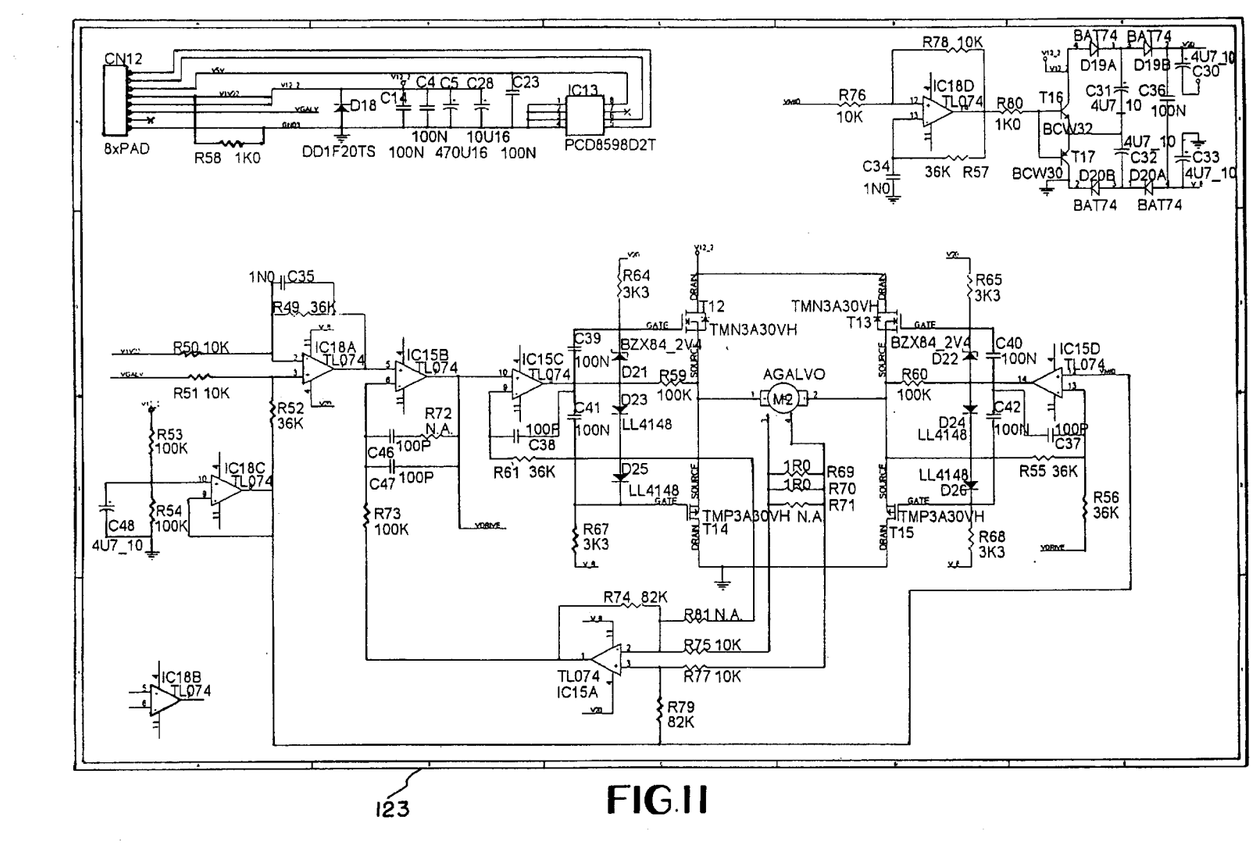
FIG. 11 shows an electric diagram of the galvanometer board
Figure 12:
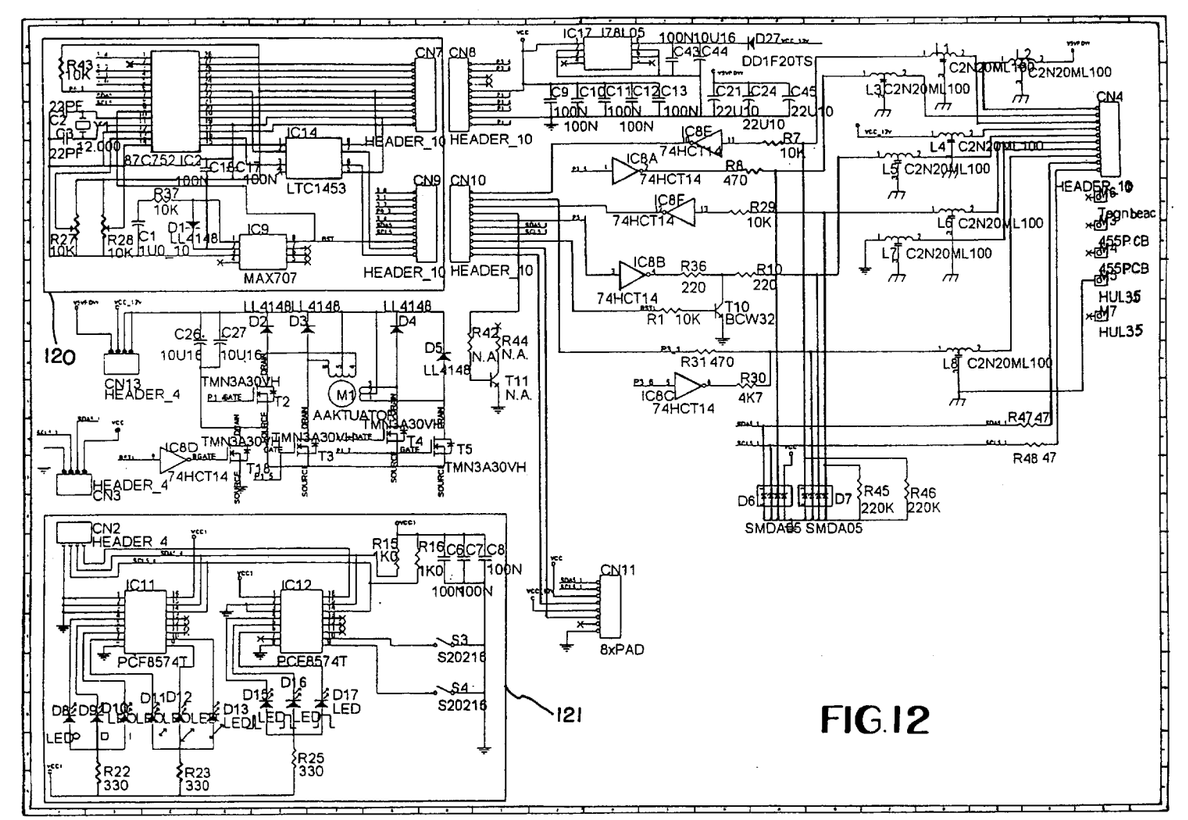
FIG. 12 shows an electric diagram of the electrical systems in the handpiece.

FIG. 11 and FIG. 12 show the electric diagrams depicting the operations of the processor IC2, e.g a 87C752 from Philips, at the controller board 120, the galvanometer M2 at the galvanometer board 123, the linear actuator M1, the push buttons and the light emitting diodes D8–D11 and D13–D17 at the display board 121 and the interconnections there between.

The processor IC2 is positioned in the handpiece and the voltage is supplied from the laser unit, e.g. a Uni-laser 450P main unit. The processor IC2 calculates the movements of the galvanometer M2 and of the linear actuator M1 from the selected treatment parameters (area, size and time). A IIC bus (not shown) is connecting the processor IC2 with the two interface integrated circuits IC11 and IC12, which may be PCF8574T from Philips.

When the handpiece is connected to the laser unit the operations of the laser unit is limited by the processor IC2 in the handpiece. The only parameters to be selected from the laser unit is the power, the pulses and the frequencies. The parameters chosen from the user interface, e.g. maximum scan time, intensity, scan size, and scan shape, are stored in an EEPROM, e.g. a PCD8598D2T from Philips, where each parameter is stored in a record, which is readable from the processor IC2. In the EEPROM IC13 also off-set values for the actuator and the galvanometer are stored.

The processor IC2 ensures that the scan is limited by the maximum treatment time chosen, and ensures that only one complete scan is performed when the pedal is activated. When the pedal is activated pin 8 at connector CN4 is high and the deflecting means are positioned to proper start positions by means of the connector CN11 to the galvanometer board BD3 and the connector CN3 to the actuator M1. The processor IC2 starts the laser unit without enabling the laser output IC8b. When the processor IC2 receives the signal 'Laser Active' from input IC8e, the processor IC2 starts to move the galvanometer M2 and the linear actuator M1, and when these reach the proper positions the output power of the laser unit is enabled IC8a. During the enabling/disabling of the power at the laser unit the mirrors are still moved, output IC8a. When the selected treatment pattern is covered, the processor IC2 stops the laser unit, that is output IC8b is low. When the pedal is released the laser unit will still be ready for treatment, and by moving to an adjacent area and depressing the pedal a large area may be treated.

What is claimed is:

1. A handpiece for tissue treatment, comprising:
   an input connector for connection of a first beam-outlet end of a first optical fiber to the handpiece and for alignment of the first optical fiber with an axis of the handpiece so that a first light beam emitted from the first beam-outlet end is transmitted substantially along the axis;
   movable first deflecting means for deflection of the first light beam into a second light beam;
   an output for emission of the second light beam towards a target surface;
   first moving means for moving the first deflecting means; and
   first deflecting control means for controlling the first moving means and being adapted to control the first moving means so that the second light beam traverses a target surface area line by line, sequentially, each line being traversed in the same direction.

2. A handpiece according to claim 1, wherein the first deflecting means comprise a first mirror.

3. A handpiece according to claim 2, wherein the first deflecting means further comprise a second mirror.

4. A handpiece according to claim 1, further comprising light switching means for preventing emission of the second light beam and light switching control means for controlling the light switching means.

5. A handpiece according to claim 1, further comprising light intensity control means for generating a control signal for transmission to a light source interconnected with the first optical fiber and controlling intensity of light emitted by the light source and transmitted through the first optical fiber.

6. A handpiece according to claim 5, further comprising a processor for control of the handpiece and comprising the first deflecting control means.

7. A handpiece according to claim 6, wherein the processor is adapted to control the light intensity control means.

8. A handpiece according to claim 1, wherein:
   the input connector is further adapted to connect a second beam-outlet end of a second optical fiber for transmission of a first visible light beam to the handpiece and for alignment of the second optical fiber with the axis of the handpiece so that the first visible light beam emitted from the second beam-outlet end is transmitted substantially in parallel with the axis, and further comprising movable second deflecting means for deflection of the first visible light beam into a second visible light beam.

9. A handpiece according to claim 8, wherein the first and the second deflecting means are identical.

10. A handpiece according to claim 8, wherein the target surface area has a size, shape and position and further has a circumference and wherein the handpiece further comprises second moving means for moving the second deflecting means and second deflecting control means for controlling the second moving means and being adapted to control the second moving means in such a way that the visible second light beam traverses at least a part of the circumference of the target surface area thereby indicating the size, shape and position of the target surface area.

11. A handpiece according to claim 10, wherein the shape of the target surface area is polygonal and the second deflecting control means is further adapted to control the second moving means in such a way that the visible second light beam is traversed along one edge of the polygon.

12. A handpiece according to claim 10, further comprising a processor for control of the handpiece and comprising the first deflecting control means.

13. A handpiece according to claim 12, wherein the processor comprises the second deflecting control means.

14. A handpiece according to claim 1, further comprising user interface means for selection of parameters of the handpiece.

15. A handpiece according to claim 14, wherein the parameters comprise a traversing velocity.

16. A handpiece according to claim 14, wherein the parameters comprise intensity of light emitted by the handpiece.

17. A handpiece according to claim 14, wherein the parameters comprise a size of the target surface area to be traversed.

18. A handpiece according to claim 14, wherein the parameters comprise a shape of the target surface area to be traversed.

19. A handpiece according to claim 14, further comprising a first button for selection of a parameter type by stepping through a set of parameter types.

20. A handpiece according to claim 19, further comprising a second button for selection of a parameter value of the parameter type currently selected by stepping through a corresponding set of parameter values.

21. A handpiece according to claim 20, further comprising a set of light emitting diodes for indication of the set of currently selected parameter values.

22. A handpiece according to claim 1, further comprising a processor for control of the handpiece and comprising the first deflecting control means.

23. A handpiece according to claim 22, wherein the processor is connected to the user interface means and is adapted to control the first moving means in accordance with the selected parameter values.

24. A handpiece according to claim 22, wherein the processor is adapted to control energy density received by the target surface when traversed by the second light beam.

25. A handpiece according to claim 24, wherein the processor is adapted to control energy density received by the target surface at a specific position as a function of the position along a desired curve traversed by the second light beam.

26. A handpiece according to claim 1, further comprising a distance member connected to the handpiece at the output with fastening means and for indicating the desired distance between the target surface and the output.

27. A handpiece according to claim 26, wherein the fastening means comprises a magnet so that the distance member can easily be disconnected from the handpiece.

28. A handpiece according to claim 1, further comprising an air tube for suction of air from the output of the handpiece whereby tissue removed from the target surface is prevented from depositing on optics of the handpiece.

29. An apparatus for tissue treatment, comprising:
a handpiece according to claim 1,
a light source for emission of the first light beam, and
the first optical fiber for transmission of the first light beam.

30. An apparatus according to claim 29, wherein the optical fiber is adapted to transmit light of a wavelength larger than or equal to 4500 nm.

31. An apparatus according to claim 30, wherein the optical fiber is adapted to transmit light of a wavelength less than 11000 nm.

32. An apparatus according to claim 31, wherein the optical fiber is adapted to transmit light of a wavelength in the range from 4500 nm to 5500 nm.

33. An apparatus according to claim 31, wherein the optical fiber is adapted to transmit light of a wavelength in the range from 10000 nm to 11000 nm.

34. An apparatus according to claim 31, wherein the optical fiber is adapted to transmit light of a wavelength substantially equal to 10600 nm.

35. An apparatus according to claim 29, wherein the optical fiber is adapted to transmit light of a wavelength larger than 190 nm.

36. An apparatus according to claim 35, wherein the optical fiber is adapted to transmit light of a wavelength less than 3000 nm.

37. An apparatus according to claim 36, wherein the optical fiber is adapted to transmit light of a wavelength in the range from 1900 nm to 2200 nm.

38. An apparatus according to claim 36, wherein the optical fiber is adapted to transmit light of a wavelength in the range from 2800 nm to 3000 nm.

39. An apparatus according to claim 38 wherein the optical fiber is adapted to transmit light of a wavelength substantially equal to 2930 nm.

40. An apparatus according to claim 29, wherein the optical fiber is a poly crystalline silver halide fiber.

41. A method of traversing a light beam across an area of a tissue, comprising the steps of:
emitting the light beam towards the tissue area;
deflecting the light beam with movable deflecting means so that the tissue is traversed by the light beam line by line, sequentially, each line being traversed in the same direction.

42. A method according to claim 41, wherein the light beam is invisible, the method further comprising the step of transmitting a visible light beam towards the tissue area utilizing the movable deflecting means.

43. A method according to claim 42, further comprising the step of traversing the visible light beam along at least a part of a circumference of the tissue area to be traversed by the invisible light beam.

44. A method according to claim 43, wherein a shape of the tissue area traversed is polygonal and the visible light beam is traversed along one edge of the polygon to be traversed by the invisible light beam.

* * * * *